US 7,435,792 B2

(12) United States Patent
Coen et al.

(10) Patent No.: US 7,435,792 B2
(45) Date of Patent: Oct. 14, 2008

(54) HYBRID PROTEINS THAT MIGRATE RETROGRADELY AND TRANSYNAPTICALLY INTO THE CNS

(75) Inventors: Laurent Coen, Montreuil (FR); Rosario Osta Pinzolas, Zaragoza (ES); Philippe Brulet, Paris (FR)

(73) Assignee: Institut Pasteur, Paris (FR)

( * ) Notice: Subject to any disclaimer, the term of this patent is extended or adjusted under 35 U.S.C. 154(b) by 512 days.

(21) Appl. No.: 09/816,467

(22) Filed: Mar. 26, 2001

(65) Prior Publication Data

US 2003/0004121 A1    Jan. 2, 2003

Related U.S. Application Data

(63) Continuation of application No. 09/129,368, filed on Aug. 5, 1998, now abandoned.

(60) Provisional application No. 60/055,615, filed on Aug. 14, 1997, provisional application No. 60/065,236, filed on Nov. 13, 1997.

(51) Int. Cl.
*C07K 1/00* (2006.01)
*A61K 39/00* (2006.01)
*C07H 21/02* (2006.01)
*C07H 21/04* (2006.01)

(52) U.S. Cl. ............... 530/350; 424/185.1; 424/192.1; 536/23.1; 536/24.1

(58) Field of Classification Search ............... 530/350; 424/185.1, 192.1; 536/23.1, 24.1
See application file for complete search history.

(56) References Cited

U.S. PATENT DOCUMENTS

| | | | |
|---|---|---|---|
| 4,479,940 A | 10/1984 | Bizzini | 514/773 |
| 4,594,336 A | 6/1986 | Bizzini | 514/2 |
| 5,082,670 A | 1/1992 | Gage et al. | 424/520 |
| 5,443,966 A * | 8/1995 | Fairweather et al. | 435/69.3 |
| 5,580,859 A | 12/1996 | Felgner et al. | 514/44 |
| 5,589,466 A | 12/1996 | Felgner et al. | 514/44 |
| 5,643,578 A | 7/1997 | Robinson et al. | 424/210.1 |
| 5,728,383 A | 3/1998 | Johnson et al. | |
| 5,728,399 A | 3/1998 | Wu et al. | 424/450 |
| 5,762,926 A | 6/1998 | Gage et al. | 424/93.21 |
| 5,780,024 A | 7/1998 | Brown et al. | 424/94.4 |
| 5,840,540 A | 11/1998 | George-Hyslop et al. | 435/69.1 |
| 6,159,948 A | 12/2000 | Robertson et al. | 514/44 |

FOREIGN PATENT DOCUMENTS

| | | |
|---|---|---|
| CA | 1152493 | 8/1983 |
| CA | 1178949 | 12/1984 |
| WO | WO 95/04151 | * 2/1995 |

OTHER PUBLICATIONS

Mueller, G. P., 1994, ARO-27890.1-LS, Order No. AD-A290 501, NTIS, p. 1-15.*

Hohne-Zell et al., 1993, FEBS Letters, vol. 336, No. 1, p. 175-180.*
Rudinger, J., 1976, Peptide Hormones, edited by Parsons, J., University Park Press, Baltimore, p. 1-7.*
Kaye et al., 1990, PNAS, USA, vol. 87,pp. 6922-6926.*
Skolnick et al., 2000, TIBTECH, vol. 18, p. 34-39.*
Fishman et al., 1996, Society for Neuroscience Abstracts, vol. 22, No. 1-3, pp. 1705.*
U.S. Appl. No. 09/501,787 of Coen et al.
D.M. Figueiredo et al.; "Delivery of Recombinant Tetanus-Superoxide Dismutase Proteins to Central Nervous System Neurons by Retrograde Axonal Transport," *Experimental Neurology*, vol. 145, pp. 546-554 (Jun. 1997).
P. Beaude et al., "Retrograde Axonal Transport of an Exogenous Enzyme Covalently Linked to B-11$_b$ Fragment of Tetanus Toxin," *J. Biochemistry*, vol. 271, pp. 87-91 (1990).
Fishman et al., "Enhanced CNS Uptake of Systemically Administered Proteins Through Conjugation with Tetanus C-fragment,"*Journal of the Neurological Sciences*, vol. 98, pp. 311-325 (1990).
J. Francis et al., "CuZn Superoxide Dismutase (SOD-1):Tetanus Toxin Fragment C Hybrid Protein for Targeted Delivery of SOD-1 to Neuronal Cells," *J. Biological Chemistry*, vol. 270, No. 25, pp. 15434-15442 (Jun. 23, 1995).
N. Fairweather et al., "Immunization of Mice Against Tetanus With Fragments of Tetanus Toxin Synthesized in *Escherichia coli*," *Infection and Immunity*, vol. 55, No. 11, pp. 2541-2545 (Nov. 1987).
P. Liston et al., "Suppression of Apoptosls in Mammalian Cells by NAIP and a Related Family of IAP Genes," *Nature*, vol. 379, pp. 349-353 (Jan. 25, 1996).
P. Boucher et al., "Neutralizing Antibodies and Immunoprotection Against Pertussis and Tetanus Obtained by Use of a Recombinant Pertussis Toxin-Tetanus Toxin Fusion Protein," *Infection and Immunity*, vol. 62, No. 2, pp. 449-456 (1994).
Montecucco et al., "Structure and Function of Tetanus and Botulinum Neurotoxins," *Quarterly Reviews of Biophysics*, 28, pp. 423-472 (1995).
Erdmann et al., "Intraaxonal and Extraaxonal Transport of $^{125}$I-Tetanus Toxin in Early Local Tetanus," *Naunyn-Schmiedeberg's Arch. Pharmacol*, 290, pp. 357-373 (1975).
Price et al., "Tetanus Toxin: Direct Evidence for Retrograde Intraaxonal Transport," *Science*, vol. 188, pp. 945-947 (1975).
Stockel et al., "Comparison Between the Retrograde Axonal Transport of Nerve Growth Factor and Tetanus Toxin in Motor, Sensory and Adrenergic Neurons," *Brain Research*, 99, pp. 1-16 (1975).
Schwab et al., "Electron Microscopic Evidence for Transsynaptic Migration of Tetanus Toxin in Spinal Cord Motoneurons: An Autoradiographic and Morphometric Study," *Brain Research*, 105, pp. 213-227 (1976).

(Continued)

*Primary Examiner*—Shin-Lin Chen
(74) *Attorney, Agent, or Firm*—Finnegan, Henderson, Farabow, Garrett & Dunner, L.L.P.

(57) ABSTRACT

The non-toxic proteolytic C fragment of tetanus toxin (TTC peptide) has the same ability to bind nerve cells and be retrogradely transported through a synapse as the native toxin. A hybrid protein encoded by the lacZ-TTC gene fusion retains the biological functions of both proteins in vivo, i.e. retrograde transynaptic transport of the TTC fragment and β-gal enzymatic activity. After intramuscular injection, enzymatic activity could be detected in motoneurons and connected neurons of the brainstem areas. This strategy is useful for the delivery of a biological activity to neurons from the periphery to the central nervous system. Such a hybrid protein can also be used to map synaptic connections between neural cells.

11 Claims, 6 Drawing Sheets

OTHER PUBLICATIONS

Helting et al., "Structure of Tetanus Toxin," *The Journal of Biological Chemistry*, 252, (1), pp. 187-193 (1977).

Eisel et al., "Tetanus Toxin: Primary Structure, Expression in *E. coli*, and Homology with Botulinum Toxins," *The EMBO Journal*, 5, (10), pp. 2495-2502 (1986).

Francis et al., "CuZn Superoxide Dismutase (SOD-1): Tetanus Toxin Fragment C Hybrid Protein for Targeted Delivery of SOD-1 to Neuronal Cells," *The Journal of Biological Chemistry*, 270, (25), pp. 15434-15442 (1995).

Kuypers et al., "Viruses as Transneuronal Tracers," *TINS*, 13, (2), pp. 71-75 (1990).

Figueiredo et al., " Delivery of Recombinant Tetanus-Superoxide Dismutase Proteins to Central Nervous System Neurons by Retrograde Axonal Transport," *Experimental Neurology*, 145, pp. 546-554 (1997).

Beaude et al., "Retrograde Axonal Transport of an Exogenous Enzyme Covalently Linked to B-II$_b$ Fragment of Tetanus Toxin," *Biochem. J.*, 271, pp. 87-91 (1990).

Fishman et al., "Enhanced CNS Uptake of Systemically Administered Proteins Through Conjunction with Tetanus C-fragment," *Journal of the Neurological Sciences*, 98, pp. 311-325 (1990).

Orkin et al., *Recommendations of the Panel to Assess the NIH Investment in Research on Gene Therapy* (Dec. 1995).

Hazinski et al., *Am. J. Respir. Cell Mol Biol.*, vol. 4(3), pp. 206-209 (1991).

Office Action mailed Jan. 12, 2006, in U.S. Appl. No. 09/501,787.

Halpern, et al., J. Infect. Immun.., vol. 58, pp. 1004-1009 (1990).

Kuypers, Trends in Neuroscience, vol. 13, pp. 71-75 (1990).

Office Action received in U.S. Appl. No. 11/375,093, mailed Feb. 20, 2008.

* cited by examiner

```
SK-TTC  -> Genes

DNA sequence    1600 b.p.                                                                          linear 1 ggaaacagctatgaccatgattacgccaagctcgaaattaaccctcactaaagggaacaaaagctggagctcggtacccg                80

81 ggccacc ATG GTT TTT TCA ACA CCA TTT TCT TAT TCT AAA AAT CTG GAT TGT TGG                        141
    1         M   V   F   S   T   P   F   S   Y   S   K   N   L   D   C   W                         18

142 GTT GAT GAA GAT ATA GAT GTT ATA TTA AAG AGT ACA ATT TTA AAT TTA GAT                            201
   19  V   D   E   D   I   D   V   I   L   K   S   T   I   L   N   L   D                             38

202 ATT AAT AAT GAT ATT ATA TCA GAT ATA TCT GGG TTT AAT CAT GTA ATA ACA TAT CCA                    261
   39  I   N   N   D   I   I   S   D   I   S   G   F   N   H   V   I   T   Y   P                     58

262 GAT GCT CAA TTG GTG CCC GGA ATA AAT GGC AAA GCA ATA CAT TTA GTA AAC AAT GAA TCT                321
   59  D   A   Q   L   V   P   G   I   N   G   K   A   I   H   L   V   N   N   E   S                 78

322 TCT GAA GTT ATA GTG CAT AAA GCT ATG GAT ATT GAA TAT GCT AGT CAT TTA AAT GAT ATG TTT            381
   79  S   E   V   I   V   H   K   A   M   D   I   E   Y   A   S   H   L   N   D   M   F             98

382 ACC GTT AGC TTT TGG TTG AGG GTT CCT AAA GTA TCT TTA GAA CAA TAT CAT CTA GAA GAT GGC TAT GGC    441
   99  T   V   S   F   W   L   R   V   P   K   V   S   L   E   Q   Y   H   L   E   D   G   Y   G    118

442 ACA AAT GAG GTA TAT TCA ATT AGC TCT ATG AAA AAA TGG ACT CAT AGT CTA AAA GAT TCC GCG TCT GGT    501
  119  T   N   E   V   Y   S   I   S   S   M   K   K   W   T   H   S   L   K   D   S   A   S   G    138

502 TGG AGT GTA TCA CTT AAA GGT AAT TTA ATA AAC TTA ACT TTT TTA ATA AAT GCT GGA GAA                561
  139  W   S   V   S   L   K   G   N   L   I   N   L   T   L   L   I   N   A   G   E                158

562 GTT AGA CAA TTT TTT ATT ACT AGG GAT TTA CCT GAT AAA TTT TCT AAT GCT TAT TTG TAT ATA AAA        621
  159  V   R   Q   F   F   I   T   R   D   L   P   D   K   F   S   N   A   Y   L   Y   I   K        178

622 TGG GTT TTT ATA ACT AAT GAT AGA TTA GAT AGA TTA TCT TCT AAT GCT AAT GCA TAT ATA AAT GGA        681
  179  W   V   F   I   T   N   D   R   L   D   R   L   S   S   A   N   A   Y   I   N   G            198

682 GTA CTT ATG GGA AGT GCA GAA ATT ACT GGT TTA GGA GCT ATT AGA GAG GAT AAT AAT ATA                741
  199  V   L   M   G   S   A   E   I   T   G   L   G   A   I   R   E   D   N   N   I               218
```

FIG. 1A

```
 742 ACA TTA AAA CTA GAT AGA TGT AAT AAT AAT CAA TAC GTT TCT ATT GAT AAA TTT AGG  801
 219  T   L   K   L   D   R   C   N   N   N   Q   Y   V   S   I   D   K   F   R   238

802 ATA TTT TGC AAA GCA TTA AAT CCA ATT GAG AAA TAC TTA TAC ACA AGT TAT TTA TCT  861
 239  I   F   C   K   A   L   N   P   I   E   K   Y   L   Y   T   S   Y   L   S   258

862 ATA ACC TTT TTA AGA GAC TTC TGG GGA AAC CCT TTA CGA TAT GAT ACA GAA TAT TTA  921
 259  I   T   F   L   R   D   F   W   G   N   P   L   R   Y   D   T   E   Y   L   278

922 ATA CCA GTA GCT TCT AGT TCT AAA GTT CAA TAT GAT ATA AAT ATA ACA GAT TAT TAT  981
 279  I   P   V   A   S   S   S   K   V   Q   Y   D   I   N   I   T   D   Y   Y   298

982 TTG ACA AAT GCG CCA TCG TAT ACT AAC GGA AAA TTG TTA CCT AAT TAT AGA AGG ATG 1041
 299  L   T   N   A   P   S   Y   T   N   G   K   L   L   P   N   Y   R   R   M   318

1042 AAT GGA CTA AAA TTT TTT ATT ATA AAA TAT ACA TCA GTA CCT AAT AAC GAA ATA TAT 1101
 319  N   G   L   K   F   F   I   I   K   Y   T   S   V   P   N   N   E   I   Y   338

1102 AAA TCA GGT GAT AAA GCC TAT AAA ATG AAA CTT GAT AGA GTA AAT AAC CTA GAG GTA 1161
 339  K   S   G   D   K   A   Y   K   M   K   L   D   R   V   N   N   L   E   V   358

1162 TAT CCG AAA GAT ATC CCT CTT TAT AAA ATG GAT GAA GCA AAT AAA CTT GAT AGA GTA 1221
 359  Y   P   K   D   I   P   L   Y   K   M   D   E   A   N   K   L   D   R   V   378

1222 GCC CCA GGT ATC CCT CTT TAT AAA ATG GAT GAT AAA AAA AGG CCA TAT GTA TCA GCA 1281
 379  A   P   G   I   P   L   Y   K   M   D   D   K   K   R   P   Y   V   S   A   398

1282 TAT TCT GTA CAA CTT TTA TAT TAT GAT AGG AAT AGG GAT CGT TTG GGA CTA TTA ATT 1341
 399  Y   S   V   Q   L   L   Y   Y   D   R   N   R   D   R   L   G   L   L   I   418

1342 CAT AAT GGT ATA AAA GGC AAC GAT ATT TTA GGA TGT TGT GAT TGG TAC AAC TGG TAC 1401
 419  H   N   G   I   K   G   N   D   I   L   G   C   C   D   W   Y   N   W   Y   438

1402 TTT AAT CAT TTA AAA GAT AAA ATT TTA CCT GTA TTT GTA CCT ACA GAT GAG 1461
 439  F   N   H   L   K   D   K   I   L   P   V   F   V   P   T   D   E   458

1462 GGA TGG ACA AAT GAT TAA acagattgatatgttcatgacatatgcccggatcctctagagtcgacctcgaggg 1535
 459  G   W   T   N   D   *  (SEQ ID NO:2)                                         464

1536 ggggcccggtacccaattcgccctatagtgagtcgtattacaattcactggccgtcgttttacaa  (SEQ ID NO:1) 1600
```

FIG. 1B

*TTC cDNA isolation:*

The TTC cDNA was isolated from a Clostridium Tetani strain using Polymerase Chain Reaction. We used a three times PCR to generate three overlapping fragments respectively of 465 bp (PCR1; primer 1:5'-CCC CCC GGG CCA CCA TGG TTT TTT CAA CAC CAA TTC CAT TTT CTT ATT C-3' (SEQ ID NO:4) & primer 2: 5'-CTA AAC CAG TAA TTT CTG-3'(SEQ ID NO:5), of 648 bp (PCR2; primer 3: 5'-AAT TAT GGA CTT TAA AAG ATT CCG C-3'(SEQ ID NO:6) & primer 4: 5'-GGC ATT ATA ACC TAC TCT TAG AAT-3'(SEQ ID NO:7) and of 338 bp (PCR3; primer 5: 5'-AAT GCC TTT AAT AAT CTT GAT AGA AAT-3'(SEQ ID NO:8) & primer 6: 5'-CCC CCC GGG CAT ATG TCA TGA ACA TAT CAA TCT GTT AA TC-3'(SEQ ID NO:9), and each fragment was sequentially cloned into pBluescript KS+ to produce plasmid pBS-TTC. The upstream primer 1 contained the Ribosome Binding Site (RBS) and translation initiation signals.

FIG. 2 dom # HYBRID PROTEINS THAT MIGRATE RETROGRADELY AND TRANSYNAPTICALLY INTO THE CNS

CROSS REFERENCE TO RELATED APPLICATIONS

This is a continuation of application Ser. No. 09/129,368, filed Aug. 5, 1998, now abandoned, which is based on provisional application Ser. No. 60/055,615, filed Aug. 14, 1997, abandoned, and provisional application Ser. No. 60/065,236, filed Nov. 13, 1997, abandoned, all of which are incorporated by reference.

BACKGROUND OF THE INVENTION

This invention relates to the use of part of tetanus toxin for delivering a composition to the central nervous system of a human or animal. This invention also relates to a hybrid fragment of tezanus toxin, a polynucleotide that hybridizes with natural tezanus toxin, and a composition containing the tetanus toxin fragment as an active molecule. Further, this invention relates to a vector comprising a-promoter and a nucleic acid sequence encoding the tetanus toxin fragment.

Tetanus toxin is produced by *Clostridium tetani* as an inactive, single, polypeptide chain of 150 kD composed of three 50 kD domains connected by protease-sensitive loops. The toxin is activated upon selective proteolytic cleavage, which generates two disulfide-linked chains: L (light, 50 kD) and H (heavy, 100 kD) [Montecucco C. and Schiavo G. Q. Rev. Biophys., (1995), 28: 423-472].

Evidence for the retrograde axonal transport of tetanus toxin to central nervous system (CNS) has been described by Erdmann et al. [Naunyn Schmiedebergs Arch Phamacol., (1975), 290:357-373], Price et al. [Science, (1975), 188:945-94], and Stoeckel et al. [Brain Res., (1975), 99:1-16]. In each of these studies, radiolabeled toxin was found inside membrane bound vesicles. Another property was the transynaptic movement of tetanus toxin that was demonstrated first by autoradiographic localization of $_{125}$I-labeled tetanus toxin in spinal cord linterneurons after injection into a muscle [Schwab and Thoenen, Brain res., (1976), 105:218-227].

The structure of this tetanus toxin has been elucidated by helting et al. [J.Biol. Chem., (1977), 252:187-193]. Papain cleaves the tetanus toxin in two fragments:

the C terminal part of the heavy chain, 451 amino acids, also called fragment C; and the other part contained the complementary portion called fragment B linked to the light chain (fragment A) via a disulfide bond.

European Patent No. EP 0 030 496 B1 showed the retrograde transport of a fragment B-II$_b$ to the CNS and was detected after injection in the median muscle of the eye in primary and second order neurons. This fragment may consist of "isofragments" obtained by clostridial proteolysis. Later, this fragment B-II$_b$ was demonstrated to be identical to fragment C obtained by papain digestion by Eisel et al. [EMBO J., 1986, 5:2495-2502].

This EP patent also demonstrated the retrograde transport of a conjugate consisting of a I$_{bc}$ tetanus toxin fragment coupled by a disulfide bond to B-II$_b$ from axonal endings within the muscle to the motoneuronal perikarya and pericellular spaces. (The I$_{bc}$ fragment corresponds to the other part obtained by papain digestion as described above by Helting et al.). There is no evidence that this conjugate was found in second order neurons. The authors indicated that a conjugate consisting of the fragment B-II$_b$ coupled by a disulfide bond to a therapeutic agent was capable of specific fixation to gangliosides and synaptic membranes. No result showed any retrograde axonal transport or a transynaptic transport for such conjugate.

Another European Patent, No. EPD 0 057 140 B1, showed equally the retrograde transport of a fragment II$_c$ to the CNS. As in the European Patent No. EP 0 030 496 31, the authors indicated that a conjugate consisting of the fragment II$_c$ and a therapeutic agent was capable of specific fixation, but no result illustrated such allegation. This fragment II$_c$ corresponds to the now called fragment C obtained by papain digestion.

Francis et al. [J. Biol. Chem., (1995), 270(25):15434-15442] just led an in vitro study showing the internalization by neurons of hybrid between SOD-1 (Cu Zn superoxide dismutase) and a recombinant C tetanus toxin fragment by genetic recombination. This recombinant C tetanus toxin fragment was obtained from Halpern group. (See ref. 11).

Moreover, Kuypers H. G. J. M and Ugolini G. [TINS, (1990), 13(2):71-75] indicated in their publication concerning viruses as transneuronal tracers that, despite the fact that tetanus toxin fragment binds to specific receptors on neuronal membranes, transneuronal labeling is relatively weak and can be detected only in some of the synaptically connected neurons.

Notwithstanding these advances in the art, there still exists a need for methods for delivering compositions into the human or animal central nervous system. There also exists a need in the art for biological agents that can achieve this result.

SUMMARY OF THE INVENTION

This invention aids in fulfilling these needs in the art. More particularly, this invention provides a method for in vivo delivery of desired composition into the central nervous system (CNS) of the mammal, wherein the composition comprises a non-toxic proteolytic fragment of tetanus toxin (TT) in association with at least a molecule having a biological function. The composition is capable of in vivo retrograde transport and transynaptic transport into the CNS and of being delivered to different areas of the CNS.

This invention also provides a hybrid fragment of tetanus toxin comprising fragment C and fragment B or a fraction thereof of at least 11 amino acid residues or a hybrid fragment of tetanus toxin comprising fragment C and fragment B or a fraction thereof of at least 11 amino acid residues and a fraction of fragment A devoid of its toxic activity corresponding to the proteolytic domain having a Zinc-binding motif located in the central part of the chain between the amino acids 225 and 245, capable of transferring in vivo a protein, a peptide, or a polynucleotide through a neuromuscular junction and at least one synapse.

Further, this invention provides a composition comprising an active molecule in association with the hybrid fragment of tetanus toxin (TT) or a variant thereof. The composition is useful for the treatment of a patient or an animal affected with CNS disease, which comprises delivering a composition of the invention to the patient or animal. In addition, the composition of this invention may be useful to elicit a immune response in the patient or animal affected with CNS, which comprises delivering a composition of the invention to the patient or animal.

Moreover, this invention provides polynucleotide variant fragments capable of hybridizing under stringent conditions with the natural tetanus toxin sequence. The stringent conditions are for example as follows: at 42° C. for 4 to 6 hours in the presence of 6×SSC buffer, 1×Denhardt's Solution, 1% SDS, and 250 µg/ml of tRNA. (1×SSC corresponds to 0.15 M NaCl1 and 0.05 M sodium citrate; 1×Denhardt's solution corresponds to 0.02% Ficoll, 0.02% polyvinyl pyrrolidone and 0.02% bovine serum albumin). The two wash steps are performed at room temperature in the presence of 0.1×SCC and 0.1% SDS.

A polynucleotide variant fragment means a polynucleotide encoding for a tetanus toxin sequence derived from the native tetanus toxin sequence and having the same properties of transport.

In addition, the invention provides a vector comprising a promoter capable of expression in muscle cells and optionally an enhancer, a nucleic acid sequence coding for the fragment of tetanus toxin of the invention or an amino acid variant fragment of the invention associated with a polynucleotide coding for a protein or a polypeptide of interest. In a preferred embodiment of the invention the promoter can be the CMV promoter and preferably the CMV promoter contained in pcDNA 3.1 (In Vitrogen, ref. V790-20), or the promoter β actin as described in Bronson S. V. et al. (PNAS, 1996), 93:9067-9072).

In addition, the invention provides a vector comprising a promoter capable of expression in neuronal cells or in precursors (such NT2(hNT) precursor cells from Stratagen reference #204101) and optionally an enhancer, a nucleic acid sequence coding for the fragment of tetanus toxin of the invention or an amino acid variant fragment of the invention associated with a polynucleotide coding for a protein or a polypeptide of interest. In a preferred embodiment of the invention the promoter can be β actin (see the above reference). These vectors are useful for the treatment of a patient or an animal infected with CNS disease comprising delivering the vector of the invention to the patient or animal. In addition, these vectors are useful for eliciting immune responses in the patient or animal.

One advantage of the present invention comprising the fragment of tetanus toxin (fragment A, B, and C) is to obtain a better transport of the fragment inside the organism compared with fragment C. Another advantage of the composition of the invention is to obtain a well defined amino acid sequence and not a multimeric composition. Thus, one can easily manipulate this composition gene therapy.

BRIEF DESCRIPTION OF THE DRAWINGS

This invention will be more fully described with reference to the drawings in which:

FIG. 1A and FIG. 1B show the DNA sequence and amino acid sequence of the TTC fragment cloned in pBS:TTC.

FIG. 2 shows the details of construct pBS:TTC.

DETAILED DESCRIPTION

Figure 3:
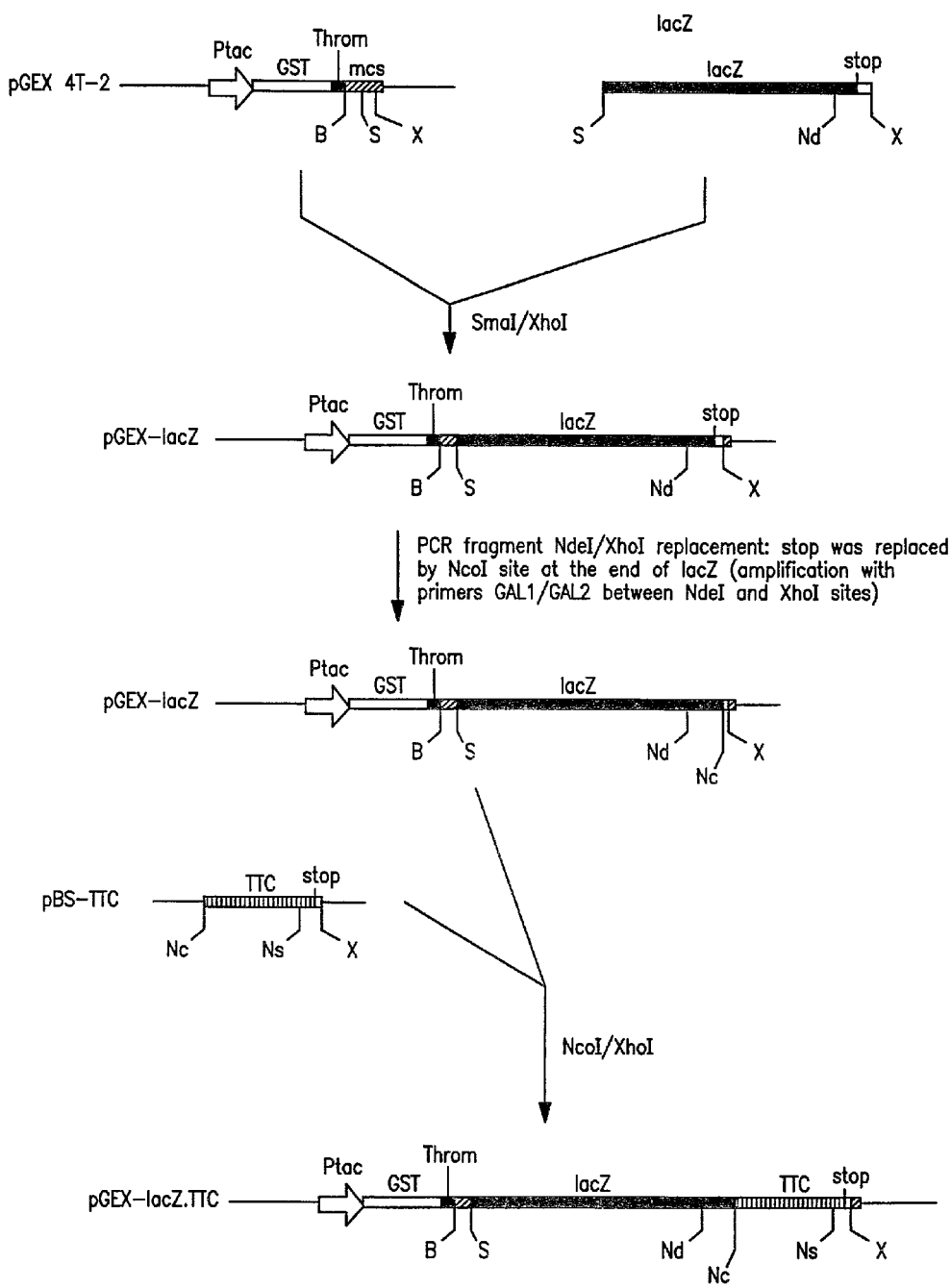
FIG. 3 depicts pGEX:lacZ-TTC construct.

Tetanus toxin is a potent neurotoxin of 1315 amino acids that is produced by *Clostridium tetani* (1, 2). It prevents the inhibitory neurotransmitter release from spinal cord interneurons by a specific mechanism of cell intoxication (for review see ref 3). This pathological mechanism has been demonstrated to involve retrograde axonal and transynaptic transport of the tetanus toxin. The toxin is taken up by nerve endings at the neuromuscular junction, but does not act at this site; rather, the toxin is transported into a vesicular compartment and travels along motor axons for a considerable distance until it reaches its targets. The transynaptic movement of tetanus toxin was first demonstrated by autoradiographic localization in spinal cord interneurons after injection into a muscle (4). However, previous studies of transynaptic passage of tetanus toxin from motoneurons were limited by the rapid development of clinical tetanus and death of the experimental animal (4, 5, 6).

A fragment of tetanus toxin obtained by protease digestion, the C fragment, has been shown to be transported by neurons in a similar manner to that of the native toxin without causing clinical symptoms (7, 8, 9, 10). A recombinant C fragment was reported to possess the same properties as the fragment obtained by protease digestion (11). The fact that an atoxic fragment of the toxin molecule was able to migrate retrogradely within the axons and to accumulate into the CNS led to speculation that such a fragment could be used as a neurotrophic carrier (12). A C fragment chemically conjugated to various large proteins was taken up by neurons in tissue culture (13) and by motor neurons in animal models (ref. 12, 14, and 15). According to the invention the fragment of tetanus toxin consists of a non-toxic proteolytic fragment of tetanus toxin (TT) comprising a fragment C and a fragment B or a fraction thereof of at least 11 amino acid residues or a non-toxic proteolytic fragment of tetanus toxin (TT) comprising a fragment C and a fragment B or a fraction thereof of at least 11 amino acids residues and a fraction of a fragment A devoid of its toxic activity corresponding to the proteolyzic domain having a zinc-binding motif located in the central part of the chain between the amino acids 225 and 245 (cf. Montecucco C. and Schiavo G. Q. Rev. Biophys., (1995), 28:423-472). Thus the fraction of the fragment A comprises, for example, the amino acid sequence 1 to 225 or the amino acid sequence 245 to 457, or the amino acid sequence 1 to 225associated with amino acid sequence 245 to 457.

The molecule having a biological function is selected from the group consisting of protein of interest, for example, for the compensation or the modulation of the functions under the control of the CNS or the spinal cord or the modulation of the functions in the CNS or the spinal cord, or protein of interest to be delivered by gene therapy expression system to the CNS or the spinal cord. The proteins of interest are, for example, the (protein SMN implicated in spinal muscular atrophy (Lefebvre et al., Cell, (1995), 80:155-165 and Roy et al., Cell, (1955), 80:167-178); neurotrophic factors, such as BDNF (Brain-derived neurotrophic factor); NT-3 (Neurotrophin-3); NT-4/5; GDNF (Glial cell-line-derived neurotrophic factor); IGF (Insulin-like growth factor) (Oppenheim, Neuron, (1996), 17:195-197 ; Thoenen et al., Exp. Neurol., (1933), 124:47-55 and Henderson et al., Adv. Neurol., (1995), 68:235-240); or PNI (protease nexin I) promoting neurite outgrowth (this factor can be used for the treatment of Alzheimer disease (Houenou et al., PNAS, (1995), 92:895-899)); or SPI3 a serine protease inhibitor protein (Safaei, Dev. Brain Res., (1997), 100: 5-12); or ICE (Interleukin-1β converting Enzyme) a factor implicated in apoptosis, to avoid apoptosis (Nagata, Cell, (1997), 88:355-365); or Bcl-2, a key intracellular regulator of programmed cell death (Jacobson, M. D. (1997), Current Biology, 7:R277-R281); or green fluorescent protein (Lang et al., Neuron, (1997), 18:857-863) as a marker; enzyme (ex : β-Gal); endonuclease like I-SceI (Choulika A., et al. (1995), Molecular and Cellular biology, 15 (4):1968-1973 or CRE (Gu H., et al. (1994), Science, 265:103-106); specific antibodies; drugs specifically directed against neurodegenerative diseases such as latero spinal amyotrophy. Several molecules can be associated with a TT fragment.

In association means an association obtained by genetic recombination. This association can be realized upstream as well as downstream to the TT fragment. The preferred mode of realization of the invention is upstream and is described in detail; a downstream realization is also contemplated. (Despite Halpern et al., J. Biol. Chem., (1993), 268(15):11188-11192, who indicated that the carboxyl-terminal amino acids contain the domain required for binding to purified gangliosides and neuronal cells.)

The desired CNS area means, for example, the tongue which is chosen to direct the transport to-hypoglossal motoneuron; the arm muscle which is chosen to direct the transport to the spinal cord motoneurons.

For this realization of transplantation of a neuron to the CNS or the spinal cord see Gage, F. H. et al. (1987), Neuroscience, 23:725-807, "Grafting genetically modified cells to the brain: possibilities for the future."

The techniques for introducing the polynucleotides to cells are described in U.S. Pat. Nos. 5,580,859 and 5,589,466, which is relied upon and incorporated by reference herein. For example, the nucleotides may be introduced by transfection in vitro before reimplantation in area of the CNS or the spinal cord.

A chemical linkage is considered for a particular embodiment of the invention and comprises the association between the TT fragment and a polynucleotide encoding the molecule of interest with its regulatory elements, such as promoter and enhancer capable of expressing said polynucleotide. Then the TT fragment allows the retrograde axonal transport and/or the transynaptic transport, and the product of the polynucleotide is expressed directly in the neurons. This chemical linkage can be covalent or not, but preferably covalent performed by thiolation reaction or by any other binding reaction as described in "Bioconjugate Techniques" from Gret T. Hermanson (Academic press, 1996).

The axonal retrograde transport begins at the muscle level, where the composition of interest is taken up at the neuromuscular junction, and migrates to the neuronal body of the motoneurons (which are also called the first order neurons) in the CNS or spinal cord. First order neurons mean neurons that have internalized the composition of interest, and thus in this case, correspond to motoneurons.

The transynaptic retrograde transport corresponds to interneuron communications via the synapses from the motoneurons, and comprises second order neurons and higher order neurons (fourth order corresponding to neurons in the cerebral cortex).

The different stages of the neuronal transport are through the neuromuscular junction, the motoneuron, also called first order neuron, the synapse at any stage between the neurons of different order, neuron of order second to fourth order, which corresponds to the cerebral cortex.

In one embodiment of this invention, it is shown that a β-gal-TTC (TT-fragment C) hybrid protein retains the biological activities of-both proteins in vivo. Therefore, the hybrid protein can undergo retrograde and transneuronal transport through a chain of interconnected neurons, as traced by its enzymatic activity. These results are consistent with those of others who used chemically conjugated TTC, or TTC fused to other proteins (12, 13, 14, 15). In these in vitro analyses, the activity of the conjugated or hybrid proteins was likewise retained or only weakly diminished. Depending on the nature of the TTC fusion partner, different types of potential applications can be envisioned. For example, this application can be used to deliver a biologically active protein into the CNS for therapeutic purposes. Such hybrid genes can also be used to analyze and map synaptically connected neurons if reporters, such as lacZ or the green fluorescent protein (GFP; 29) gene, were fused to TTC.

The retrograde transport of the hybrid protein may be demonstrated as follows. When injected into a muscle, β-gal activity rapidly localized to the somata of motoneurons that innervate the muscle. The arborization of the whole nerve, axon, somata and dendrites can easily be visualized. However, in comparison to the neurotropic viruses, the extent of retrograde transneuronal transport of the hybrid protein from the hypoglossal neurons indicates that only a subset of interconnected neurons is detected, although most areas containing second-order interneurons have been identified by the β-gal-TTC marker. Transneuronal uptake is mostly restricted to second order neurons. In such experiments, when a limited amount of a neuronal tracer is injected into a muscle or cell, only a fraction will be transported through a synapse, thereby imposing an experimental constraint on its detection. Presently, the most efficient method, in terms of the extent of transport, relies on neurotropic viruses. Examples include: alpha-herpes viruses, such as herpes simplex type 1 (HSV-1), pseudorabies virus (PrV), and rhabdoviruses (24, 25). Viral methods are very sensitive because each time a virus infects a new cell, it replicates, thereby amplifying the signal and permitting visualization of higher order neurons in a chain. Ultimately, however, one wants to map a neuronal network in an in vivo situation such as a transgenic animal. Here, the disadvantage of viral labeling is its potential toxicity. Most viruses are not innocuous for the neural cell, and their replication induces a cellular response and sometimes cell degeneration (24). Furthermore, depending on experimental conditions, budding of the virus can occur leading to its spread into adjoining cells and tissues.

Differences in mechanisms of transneuronal migration could also account for the restricted number of neurons labeled by β-gal-TTC. Matteoli et al have provided strong evidence that the intact tetanus toxin crosses the synapses by parasitizing the physiological process of synaptic vesicle recycling at the nerve terminal (22). The toxin probably binds to the inner surface of a synaptic vesicle during the time the lumen is exposed to the external medium. Vesicle endocytosis would then presumably provide the mechanism for internalization of the toxin. Because the TTC fragment is known to mimic the migration of the toxin in vivo, it could therefore direct the fusion protein along a similar transynaptic pathway. If this hypothesis is confirmed, it would strongly suggest that synaptic activity is required for the transneuronal transport of β-gal-TTC. Therefore, only active neuronal circuits would be detected by the hybrid protein. The possible dependence of β-gal-TTC on synaptic vesicle exocytosis and endocytosis could be further investigated, since techniques are now available to record synaptic activity in neural networks in vitro (30). In contrast, the transneuronal pathway of neurotropic viruses has not yet been elucidated and could be fundamentally different, involving virus budding in the vicinity of a synapse. Finally, the transneuronal transport of the hybrid protein might depend on a synaptic specificity, although the tetanus toxin is not known to display any (7, 23). It is therefore likely that a virus would cross different or inactive synapses. In summary, the restricted spectrum of interneuronal transport, in addition to its non-toxicity, make the β-gal-TTC hybrid protein a novel and powerful tool for analysis of neural pathways.

One advantage of the fusion gene of the invention for neuronal mapping is that it derives from a single genetic entity that is amenable to genetic manipulation and engineering. Several years ago, a technique based on homologous recombination in embryonic stem cells was developed to specifically replace genes in the mouse (31, 32). This method generates a null mutation in the substituted gene, although in a slightly modified strategy, a dicistronic messenger RNA can also be produced (33, 34). When a reporter gene, such as E.coli lacZ, is used as the substituting gene, this technique provides a means of marking the mutated cells so that they can be followed during embryogenesis. Thus, this technique greatly simplifies the analysis of both the heterozygote expression of the targeted gene as well as the phenotype of null (homozygous) mutant animals.

Another advantage of this invention is that the composition comprising the fusion gene may encode an antigen or antigens. Thus, the composition may be used to elicit an immune response in its host and subsequently confer protection of the host against the antigen or antigens expressed. These immunization methods are described in Robinson et al., U.S. Pat. No. 5,43,578, which is herein incorporated by reference. In particular, the method of immunizing a patient or animal host comprises introducing a DNA transcription unit encoding comprising the fusion gene of this invention, which encodes a desired antigen or antigens. The uptake of the DNA transcription unit by the host results in the expression of the desired antigen or antigens and the subsequent elicitation of humoral and/or cell-mediated immune responses.

Neural cells establish specific and complex networks of interconnected cells. If a gene mere mutated in a given neural cell, we would expect this mutation to have an impact on the functions of other, interconnected neural cells. With these considerations in mind, a genetic marker that can diffuse through active synapses would be very useful in analyzing the effect of the mutation. In heterozygous mutant animals, the cells in which the targeted gene is normally transcribed could be identified, as could the synaptically connected cells of a neural network. In a homozygous animal, the impact of the mutation on the establishment or activity of the neural network could be determined. The feasibility of such an in vivo approach depends critically on the efficiency of synaptic transfer of the fusion protein, as well as its stability and cellular localization.

Another extension of the invention is to gene therapy applied to the CNS. This invention provides for uptake of a non-toxic, enzyme-vector conjugate by axon terminals and conveyance retrogradely to brainstem motoneurons. A selective retrograde transynaptic mechanism subsequently transports the hybrid protein into second-order connected neurons. Such a pathway, which by-passes the blood-brain barrier, can deliver macromolecules to the CNS. In fact, pathogenic agents, such as tetanus toxin and neurotropic viruses, are similarly taken up by nerve endings, internalized, and retrogradely transported to the nerve cell somata. In such a scenario, the lacZ reporter would be replaced by a gene encoding a protein that provides a necessary or interesting activity and/or function. For example, the human CuZn superoxide dismutase, SOD-1, and the human enzyme β-N-acetylhexosaminidase A, HexA, have been fused or chemically coupled to the TTC fragment (13, 16), and their uptake by neurons in vitro was considerably increased and their enzymatic functions partially conserved. Combined with the in vivo experiments described here using β-gal-TTC, a gene therapy approach based on TTC hybrid proteins appears to be a feasible method of delivering a biological function to the CNS. However, ways have to be found to target the TTC hybrid proteins, which are likely to be sequestrated into vesicles, to the appropriate subcellular compartment. Such a therapeutic strategy could be particularly useful for treating neurodegenerative and motoneuron diseases, such as amyotrophy lateral sclerosis (ALS, 35), spinal muscular atrophies (SMA, 36, 37), or neurodegenerative lysosomal storage diseases (38, 39). Injection into selected muscles, even in utero, could help to specifically target the appropriate neurons. In addition, such an approach would avoid the secondary and potentially toxic effects associated with the use of defective viruses to deliver a gene (40, 41).

EXAMPLES

Example 1

Figure 4:
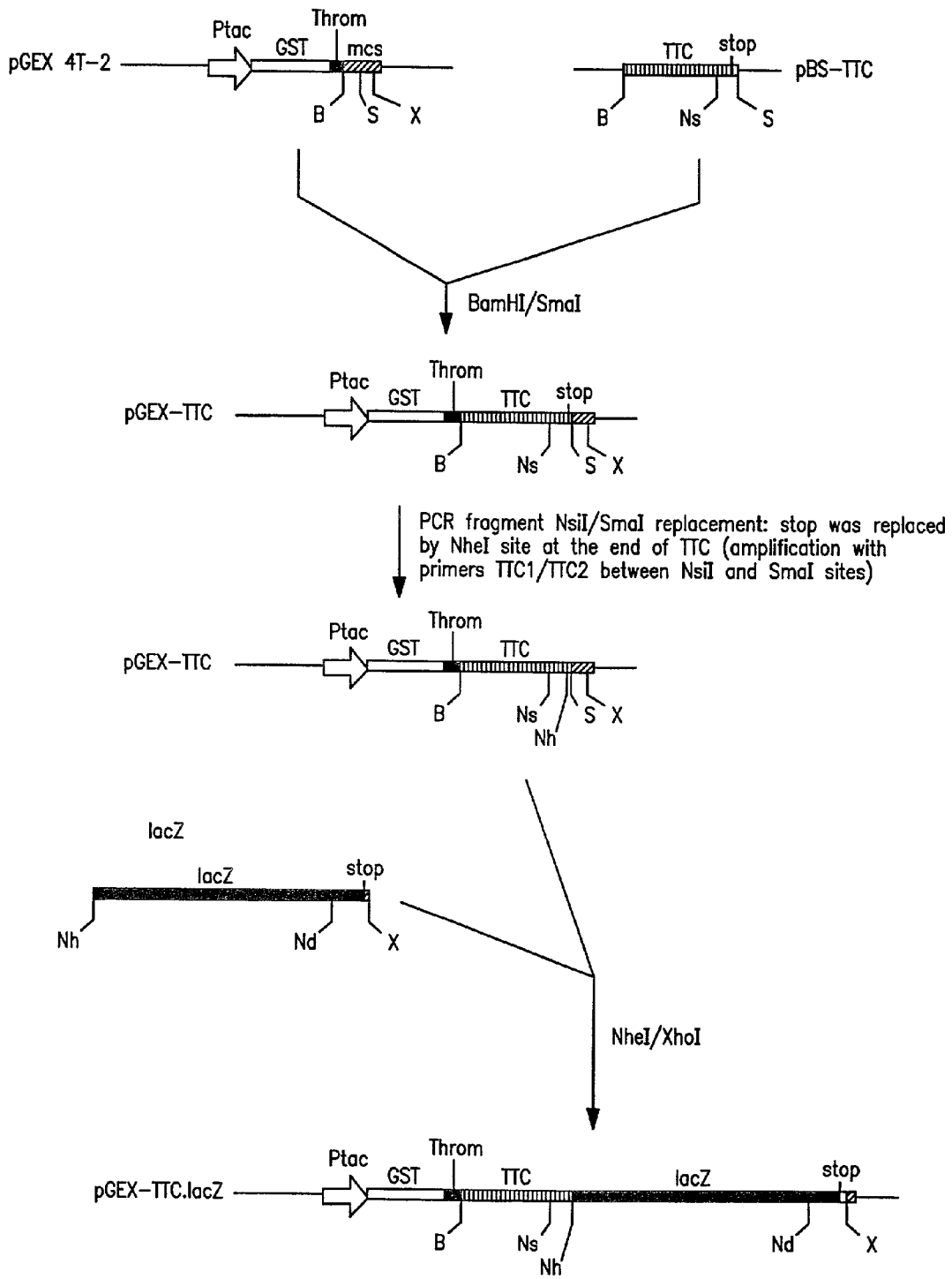
FIG. 4 shows construct pGEX:TTC-lacZ.
Figure 5:
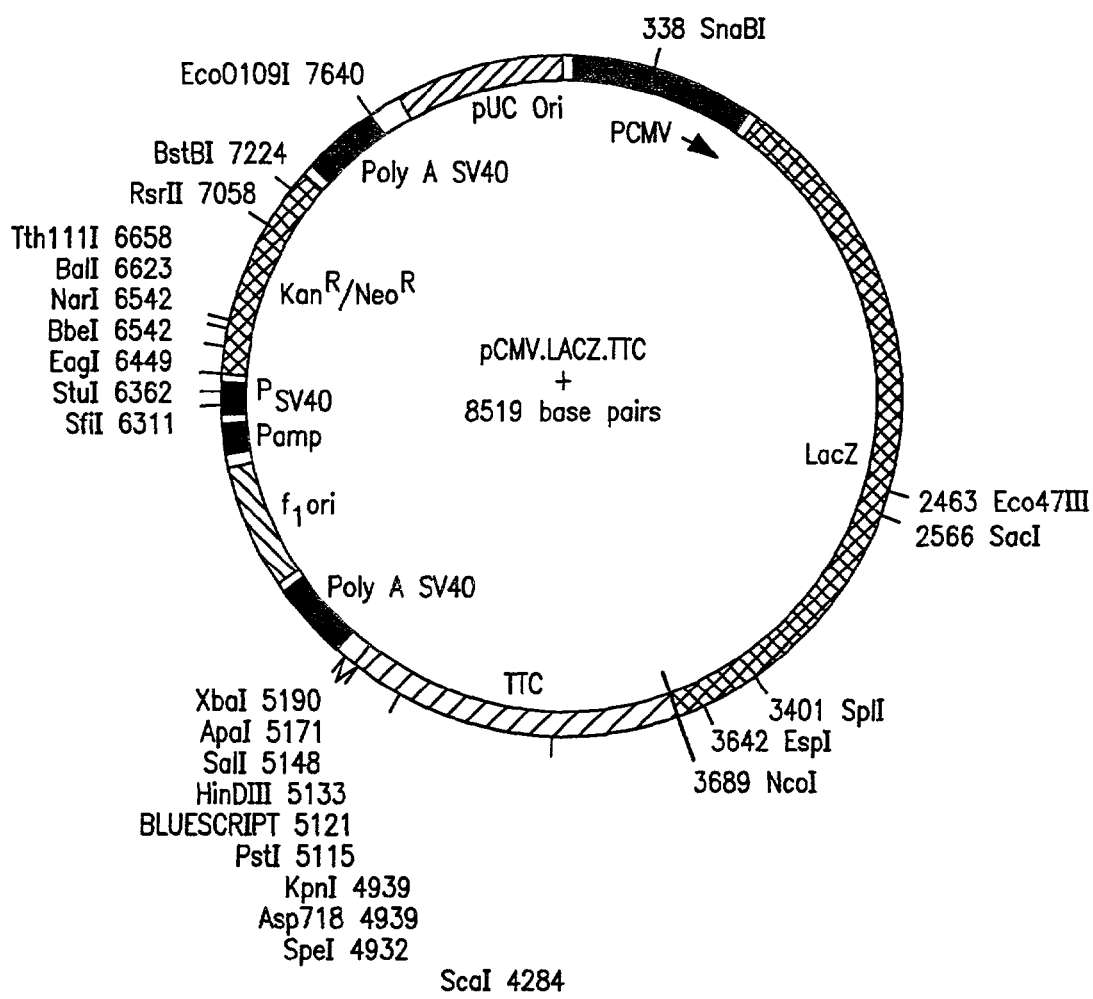
FIG. 5 depicts the details of the construct pCMV:lacZ-TTC.

Plasmid Constructions (A) TTC cloning:

Full length TTC DNA was generated from the genomic DNA from the *Clostridium Tetani* strain (a gift from Dr. M. Popoff, Institut Pasteur) using PCR. Three overlapping fragments were synthesized: PGRI of 465 bp (primer 1: (SEQ ID NO:4) 5'-CCC CCC GGG CCA CCA TGG TTT TTT CAA CAC CAA TTC CAT TTT CTT ATT C-3' and primer 2: (SEQ ID NO: 5) 5'-CTA AAC CAG TAA TTT CTG-3'), PCR2 of 648 bp (primer 3: (SEQ ID NO:6) 5'-AAT TAT GGA CTT TAA AAG ATT CCG C-3' and primer 4: (SEQ ID NO: 7) 5'-GGC ATT ATA ACC TAC TCT TAG AAT-3') and PGR3 of 338 bp (primer 5: (SEQ ID NO: 8) 5'-AAT GCC TTT AAT AAT CTT GAT AGA AAT-3' and primer 6: (SEQ ID NO: 9) 5'-CCC CCC GGG CAT ATG TCA TGA ACA TAT CAA TCT GTT TAA TC-3'). The three fragments were sequentially introduced into pBluescript KS+ (Stratagene) to give pBS:TTC plasmid. The upstream primer 1 also contains an optimized eukaryotic Ribosome Binding Site (RBS) and translational initiation signals. Our TTG fragment (462 amino acids) represents the amino acids 854-1315 of tetanus holotoxin, i.e. the carboxy-terminal 451 amino acids of the heavy chain, which constitute the fragment C plus 11 amino acids of the heavy chain that immediately precede the amino terminus of the fragment C. The DNA sequence and amino acid sequence of the TTC fragment cloned in pBS:TTC is shown in FIG. 1. The construct pBS:TTC is shown in FIG. 2.

(B) pGEX:lacZ-TTC:

pGEX:lacZ was obtained by cloning a SmaI/XhoI lacZ fragment from the pGNA vector (a gift from Dr. H. Le Mouellic) into pGEX 4T-2 (Pharmacia). PCR was used to convert the lacZ stop codon into an NcoI restriction site. Two primers (upstream: (SEQ ID NO: 12) 5'-CTG AAT ATC GAC GGT TTC CAT ATG-3' and downstream: (SEQ ID NO: 13) 5'-GGC AGT CTC GAG TCT AGA CCA TGG CTT TTT GAC ACC AGA C-3') were used to amplify the sequence between NdeI and XhoI, generating pGEX:lacZ(NcoI) from pGEX:lacZ. pGEX:lacZ-TTC was obtained by insertion of the TTC NcoI/XhoI fragment into pGEX:lacZ(NcoI), fusing TTC immediately downstream of the lacZ coding region and in the same reading frame. FIG. 3 shows the details of the nGEX:lacZ-TTC construct.

(C) pGEX: TTC-lacZ:

pBS:TTC was modified to change NcoI into a BamHI restriction site (linker (SEQ ID NO: 14) 5'-CAT GAC TGG GGA TCC CCA GT-3') at the start of the TTC DNA, to give pBS:TTC(BamHI) plasmid. pGEX:TTC was obtained by cloning The TTC BamHI/SmaI fragment from pBS:TTC (BamHI) into pGEX 4T-2 (Pharmacia). PCR was used to convert the TTC stop codon into an NheI restriction site. Two primers (upstream: (SEQ ID NO: 15) 5'-TAT GAT AAA AAT GCA TCT TTA GGA-3' and downstream: (SEQ ID NO: 16) 5'-TGG AGT CGA CGC TAG CAG GAT CAT TTG TCC ATC CTT C-3') were used to amplify the sequence between NsiI and SmaI, generating pGEX:TTC(NheI) from pGEX: TTC. The lacZ cDNA from plasmid pGNA was modified in its 5' extremity to change SacII into an NheI restriction site (linker 5'-GCT AGC GC-3'). pGEX:TTC-lacZ was obtained by insertion of the lacZ NheI/XhoI fragment into pGEX:TTC (NheI), fusing lacZ immediately downstream of the TTC coding region and in the same reading frame. The details of the construct of pGEX:TTC-lacZ are shown in FIG. 4.

(D) pCMV:lacZ-TTC:

pCMV vector was obtained from pGFP-C1 (Clontech laboratories) after some modifications: GFP sequence was deleted by a BglII/NheI digestion and relegation, and SacII in the polylinker was converted into an AscI restriction site (linkers 5'-GAT ATC GGC GCG CCA GC-3' (SEQ ID NO: 17) and (SEQ ID NO: 18) 5'-TGG CGC GCC GAT ATC GC-3').

pBluescript KS+ (Stratagene) was modified to change XhoI into an AscI restriction site (linker (SEQ ID NO: 19) 5'-TCG ATG GCG CGC CA-3'), giving pBS(AscI) plasmid. pBS:lacZ-TTC was obtained by cloning a XmaI lacZ-TTC fragment from pGEX:lacZ-TTC into pBS(AscI). pCMV: lacZ-TTC was obtained by insertion of the lacZ-TTC XmnI/AscI fragment into pCMV vector at the XhoI and AscI sites (XhoI and XmnI was eliminated with the clonage), putting the fusion downstream of the CMV promotor. FIG. 8 shows the details of the construct pCMV:lacZ-TTC. Plasmid pCMV:lacZ-TTC was deposited on Aug. 12, 1997, at the Collection Nationale de Cultures de Microorganisms (CNCM), Institut Pasteur, 25, Rue du Docteur Roux, F-75724, Paris Cedex 15, France, under Accession No. 1-1912.

Example 2

Purification of the Hybrid Protein

The *E. coli* strain SR3315 (a gift from Dr. A. Pugsley, institut Pasteur) transfected with pGEX:lacz-TTC was used for protein production. An overnight bacterial culture was diluted 1:100 in LB medium containing 100 µg/ml ampicillin, and grown for several hours at 32° C. until an OD of 0.5 was reached. Induction from the Ptac promoter was achieved by the addition of 1 mM IPTG and 1 mM $MgCl_2$ and a further 2 hrs incubation. The induced bacteria were pelleted by centrifugation for 20 min at 3000 rpm, washed with PBS and resuspended in lysis buffer containing 0.1M Tris pH 7.8, 0.1M NaCl, 20% glycerol, 10 mM EDTA, 0.1% Triton-X100, 4 mM DTT, 1 mg/ml lysosyme, and a mixture of anti-proteases (100 µg/ml Pefablok, 1 µg/mil leupeptin, 1 µg/ml pepstatin, 1 mM benzamidine). After cell disruption in a French Press, total bacterial lysate was centrifuged for 10 min at 30000 rpm. The resulting supernatant was incubated overnight at 4° C. with the affinity matrix Glutathione Sepharose 4B (Stratagene) with slow agitation. After centrifugation for 5 min at 3000 rpm, the matrix was washed three times with the same lysis buffer but without lysosyme and glycerol, and then three times with PBS. The resin was incubated overnight at 4° C. with Thrombin (10 U/ml; Sigma) in PBS in order to cleave the β-gal-TTC fusion protein from the Glutatione-S-transferase (GST) sequence and thereby elute it from the affinity column. Concentration of the eluted fusion protein was achieved by centrifugation in centricon X-100 tubes (Amicon; 100,000 MW cutoff membrane).

Purified hybrid protein was analyzed by Western blotting after electrophoretic separation in 8% acrylamide SDS/PAGE under reducing conditions followed by electrophoretic transfer onto nitrocellulose membranes(0.2 mm porosity, Bio-Rad). Immunodetection of blotted proteins was performed with a Vectastain ABC-alkaline phosphatase kit (Vector Laboratories) and DAB color development. Antibodies were used as follows: rabbit anti-β-gal antisera (Capel), dilution 1:1000; rabbit anti-TTC antisera (Calbiochem), dilution 1:20000. A major band with a relative molecular mass of 180 kDa corresponding to the β-Gal-TTC hybrid protein was detected with both anti-β-Gal anti-TTC antibodies.

Example 3

Binding and Internalization of Recombinant Protein in Differentiated 1009 cells

The 1009 cell line was derived from a spontaneous testicular teratocarcinoma arising in a recombinant inbred mouse strain (129×B6) (17). The 1009 cells were grown in Dulbecco's modified Eagle's medium (DMEM) containing 10% fetal calf serum and passaged at subconfluence. In vitro differentiation with retinoic acid and cAMP was performed as described (18). Eight days after retinoic acid treatment, cells were used for the internalization experiments with either the hybrid protein or β-gal.

Binding and internalization of the β-Gal-TTC fusion were assessed using a modified protocol (16). Differentiated 1009 cells were incubated for 2 hrs at 37° C. with 5 µg/ml of β-Gal-TTC or β-Gal protein diluted in binding buffer (0.25% sucrose, 20 mM Tris acetate 1 mM CaC12, 1 mM $MgCl_2$, 0.25% bovine serum albumin, in PBS). The cells were then incubated with 1 µg/ml Pronase E (Sigma) in PBS for 10 min at 37° C., followed by washing with proteases inhibitors diluted in PBS (100 µg/ml Pefablok, 1 mM benzamidine).

The cells were fixed with 4% formalin in PBS for 10 min at room temperature (RT) and then washed extensively with PBS. β-gal activity was detected on fixed cells by an overnight staining at 37° C. in X-Gal solution (0.8 mg/ml X-Gal, 4 mM potassium ferricyanide, 4 mM potassium ferrocyanide, 4 mM $MgCl_2$ in PBS). For electron microscopy, the cells were further fixed in 2.5% glutaraldehyde for 18 hrs, and then processed as described (19).

For immunohistochemical labeling, cells were fixed with 4% paraformaldehyde in PBS for 10 min at RT then washed extensively with PBS, followed by a 1 hr incubation at RT with 2% BSA/0.02% Triton X-100 in PBS. Cells were co-incubated in primary antibodies diluted in 2% BSA/0.02% Triton X-100 in PBS for 2 hrs at RT. Antibodies used were a mouse anti-neurofilament antibody (NF 200 Kd, dilution 1:50; Sigma) or the rabbit anti-TTC antibody (dilution 1:1000). The labeling was visualized using fluorescent secondary antibodies: Cy3, goat anti-rabbit IgG (dilution 1:500; Amersham) or anti-mouse IgG with extravidin-FITC (dilution 1:200; Sigma). Cells were mounted in moviol and visualized with epifluorescence.

Example 4

In Vivo Recombinant Protein Injection 14-week old B6D2F1 mice were obtained from IFFA-CREDO. The animal's tongue muscle was injected using an Hamilton syringe (20 µl per animal) while under general anesthesia with 3% Avertin (15 µl/g of animal). The protein concentration was 0.5 to 5 µg/µl in PBS; therefore, mice received approximately 10 to 100 µg per injection. Animals were kept alive for 12 hrs to 48 hrs post-injection to permit migration of the injected protein, and in no case were any tetanus symptoms detected. The mice were sacrificed by intracardiac perfusion with 4% paraformaldehyde in PBS while under deep anesthesia. Brains were harvested, rinsed in PBS and incubated in 15% sucrose overnight at 4° C., then mounted in tissue-tek before sectioning, 15 μm thick slices using a cryostat.

Example 5

Histology, Immunohistology, and X-Gal Staining

For in toto X-Gal staining of the dissected brain and tongue, mice (10 animals) were sacrificed and fixed as described above. The brain was further cut with a scalpel along a median plane and directly incubated for 12 hrs in X-Gal solution.

For immunohistology, sections were incubated In a 1:5000 dilution of anti-TTC antibody in 2% BSA/0.02% Triton X-100 in PBS overnight at 4° C. after nonspecific antibody binding sites were blocked by a 1 hr incubation in the same buffer. Antibody detection was carried out using the Vectastain ABC-alkaline phosphatase kit with DAB color development. For X-Gal staining, sections were incubated in X-Gal solution and counterstained for 30 sec with hematoxylin 115 (v/v) in PBS. Histology on adjacent sections was done after X-Gal staining, using a 30 sec incubation in hematoxylin/thionin solution. All sections were mounted in moviol before eight microscopy analysis.

Example 6A

Internalization of the β-gal-TTC Fusion Protein by Neurons in Vitro

Differentiation of 1009 cells with retinoic acid and cAMP in vitro yields neuronal and glial cells (18, 20). X-Gal staining or immunolabeling were performed after incubation with the β-gal-TTC fusion protein or with either the β-gal or TTC proteins alone. Only when the hybrid protein was incubated with differentiated 1009 cells was a strong X-Gal staining detected in cells having a neuronal phenotype. No signal was detected when β-gal alone was incubated under the same conditions. A similar X-Gal staining pattern was obtained after pronase treatment of the cells to remove surface bound proteins, indicating that the hybrid protein had been internalized. The intracellular localization of the hybrid protein was further confirmed by electron microscopic analysis of X-Gal-stained cells. Furthermore, the enzymatic activity observed in axons seemed to be localized in vesicles associated with filaments, which is in agreement with previous work on TTC fragment or native tetanus toxin (14, 21, 22). Co-labeling with anti-TTC and anti-neurofilament antibodies revealed that β-gal activity co-localized with TTC fragment in neuronal cells. No glial cells were labeled with either antibody.

Example 6B

Internalization of the TTC-β-Gal Fusion Protein by Neurons in Vitro

The method used for the internalization was identical to that described in Example 6 above. The results show efficiently internalization of the hybrid as in Example 6 above.

Example 7

Retrograde Transport of the Hybrid Protein in Vivo

To study the behavior of the β-gal-TTC protein in vivo, the hybrid protein was tested in a well characterized neuronal network, the hypoglossal system. After intramuscular injection of β-gal-TTC protein into the mouse tongue, the distribution of the hybrid protein in the CNS was analyzed by X-Gal staining. Various dilutions of the protein were injected and sequential time points were analyzed to permit protein transport into hypoglossal motoneurons (Xll), and its further transneuronal migration into connected second order neurons.

A well-defined profile of large, apparently retrogradely labeled neurons was clearly evident in the hypoglossal structure, analyzed in toto at 12 hrs post-injection. A strong labeling was also apparent in the hypoglossal nerve (Xlln) of the tongue of the injected mice. At the level of muscle fibers, button structures were observed that might reflect labeling of neuromuscular junctions where the hybrid protein was internalized into nerve axons. These data demonstrate that the β-gal-TTC hybrid protein can migrate rapidly by retrograde axonal transport as far as motoneuron cell bodies, after prior uptake by nerve terminals in the tongue. This specific uptake and the intraaxonal transport are similar to the properties that have been described for the native toxin (6, 21, 23).

Transport of the hybrid protein was examined in greater detail by analyzing X-Gal-stained brain sections. Motoneurons of the hypoglossal nucleus became labeled rapidly, with 12 hrs being the earliest time point examined. Most of the label was confined to neuronal somata, the cell nuclei being unlabeled. The intensity of the labeling depends upon the concentration of the β-gal-TTC protein injected: when 10 μg of protein was injected, only the hypoglossal somata were detected, whereas with 25 to 50 μg a fuzzy network of dendrites was visualized; transsynaptic transfer was detected with 100 μg of hybrid protein. An identical distribution of label was observed then brain sections were immunostained with an anti-TTC antibody, demonstrating that β-gal and TTC fragment co-localize within cells. Finally, injection of β-gal alone did not result in labeling of the hypoglossal nuclei and therefore confirms that transport of the hybrid protein is TTC-dependent. Labeling with an anti-TTC antibody was less informative than detection of β-gal activity; for instance, the nerve pathway to the brain could not be visualized by anti-TTC immunostaining. At 18 hrs post-injection, labeling was observed in the hypoglossal nuclei: all motoneuron cell bodies and the most proximal part of their dendrites were every densely stained. In contrast, no labeling was ever detected in glial cells adjoining Xll motoneurons or their axons. Our results are in accordance with others who reported an identical pattern of immunolabeling after injection of the TTC fragment alone (9). Transneuronal transfer is detectable after 24 hrs. An additional 24 hrs and beyond did not yield a different staining.

Example 8

Transneuronal Transport of the Hybrid Protein

Second order interneurons, as well as higher order neurons that synapse with the hypoglossal motoneurons, have been extensively analyzed using conventional markers, such as the wheat germ agglutinin-horseradish peroxidase complex (WGA-HRP) or neurotropic viruses such as alpha-herpes (24) and rhabdoviruses (25). An exhaustive compilation of regions in the brain that synaptically connect to the hypoglossal nucleus has also been described recently (25). In this invention, the distribution of the β-gal-TTC fusion depended on the initial concentration of protein injected into the muscle and the time allowed for transport after injection. Up to 24 hrs post-injection, labeling was restricted to the hypoglossal nuclei. After 24 hrs, the distribution of second order transneuronally labeled cells in various regions of the brain was consistent and reproducible. Even at longer time points (e.g. 48 hrs), labeling of the hypoglossal nucleus remained constant. At higher magnification, a discrete and localized staining of second-order neurons was observed, suggesting that the hybrid protein had been targeted to vesicles within cell somata, synapses and axons. A similar patchy distribution was previously described for tetanus toxin and TTC fragment alone (14, 21, 22).

Intense transneuronal labeling was detected in the lateral reticular formation (LRF), where medullary reticular neurons have been reported to form numerous projections onto the hypoglossal nucleus (26, 27). β-gal activity was detected bilaterally in these sections. Label led LRF projections formed a continuous column along the rostrocaudal axis, beginning lateral to the hypoglossal nucleus, with a few neurons being preferentially stained in the medullary reticular dorsal (MdD) and the medullary reticular ventral (MdV) nuclei. This column extends rostrally through the medulla, with neurons more intensely labeled in the parvicellular reticular nucleus (PCRt, caudal and rostral). After 48 hrs, cells in MdD and PCRt were more intensely stained. A second bilateral distribution of medullary neurons projecting to the hypoglossal nucleus was detected in the solitary nucleus (Sol) but the labeling was less intense than in the reticular formation, presumably because relatively few cells of the solitary nucleus project onto the hypoglossal nucleus (26). However, no labeling was found in the spinal trigeminal nucleus (Sp5), which has also been shown to project onto the hypoglossal nucleus (26). Transynaptic transport of the β-gal-TTC protein was also detected in the pontine reticular nucleus caudal (PnC), the locus coeruleus (LC), the medial vestibular nucleus (MVe) and in a few cells of the inferior vestibular nucleus (IV). These cell groups are known to project onto the hypoglossal nucleus (25), but their labeling was weak, probably because of the greater length of their axons. A few labeled cells were observed in the dorsal paragigantocellular nucleus (DPGi), the magnocellular nucleus caudal (RMc), and the caudal raphe nucleus (R); their connections to the hypoglossal nucleus have also been reported (25). Finally, labeled neurons were detected bilaterally in midbrain projections, such as those of the mesencephalic trigeminal nucleus (Me5), and a few neurons were stained in the mesencenhalic central gray region (CG). These latter nuclei have been typed as putative third order cell groups related to the hypoglossal nucleus (25).

Neurons in the motor trigeminal nucleus (Mo5) and the accessory trigeminal tract (Acs5) were also labeled, along with a population of neurons in the facial nucleus (N7). However, interpretation of this labeling is more ambiguous, since it is known that motoneurons in these nuclei also innervate other parts of the muscular tissue, and diffusion of the hybrid protein might have occurred at the point of injection. Conversely, these nuclei may have also projected to the tongue musculature via nerve XII, since neurons in N7 have been reported to receive direct hypoglossal nerve input (28). This latter explanation is consistent with the fact that labeling in these nuclei was detected only after 24 hrs; however, this point was not further investigated.

Altogether, the data summarized in Table 1 clearly establish transneuronal transport of the β-gal-TTC fusion protein from the hypoglossal neurons into several connected regions of the brainstem.

TABLE 1

Transneuronal transport of the lacZ-TTC fusion from the XII nerve: labeling of different cells types in the central nervous system.

| Cell groups | 12-18 hrs | 24-48 hrs |
|---|---|---|
| First order neurons | | |
| First category: | ++ | +++ |
| XII, hypoglossal motoneurons | | |
| Second category: | | |
| N7, facial nu | − | ++ |
| Mo5, motor trigeminal nu | − | ++ |
| Acs5, accessory trigeminal nu | − | + |
| Second order cell groups | | |
| MdD, medullary reticular nu, dorsal | − | ++ |
| MdV, medullary reticular nu, ventral | − | +/− |
| PCRt, parvicellular reticular nu, caudal | − | ++ |
| PCRt, parvicellular reticular nu, rostral | − | ++ |
| Sol, solitary tract nu | − | + |
| DPGi, dorsal paragigantocellular nu | − | +/− |
| PnC, pontine reticular nu, caudal | − | + |
| RMc, magnocellular reticular nu | − | +/− |
| R, caudal raphe nu | − | +/− |
| MVe, medial vestibular nu | − | + |
| IV, inferior vestibular nu | − | +/− |
| LC, locus coeruleus | − | + |
| Me5, mesencephalic trigeminal nu (*) | − | + |
| CG, mesenphalic central gray (*) | − | +/− |

(*) Represents second order cell groups that also contain putative third order neurons (see text).
−, no labeling;
+ to +++, increased density of label;
+/− weak labeling.
16 animals were analysed for the 12-18 hrs p.i. data;
6 animals were analysed for the 24-48 hrs p.i. data.

REFERENCES

The following publications, which have been cited herein, are relied upon and incorporated by reference in their entireties herein.

1. Eisel, U., Jarausch, W., Goretzki, K., Henschen, A., Engels, J., Weller, U., Hudel, M., Habermann, E. & Niemann, H. (1986) *EMBO J.* 5, 2495-2502.
2. Fairweather, N. F. & Lyness, V. A. (1986) *Nucleic Acids Res.* 14, 7809-7812.
3. Montecucco, O. & Schiavo, G. (1995) *Quart. Rev. Biophys.* 28, 423-472.
4. Schwab, M. E. & Thoenen, H. (1976) *Brain Res.* 105, 213-227.
5. Schwab, M. E. & Thoenen$_1$ H. (1977) *Brain Res.* 122, 459-474
6. Price, D. L., Griffin, J. W. & Peck. K. (1977) *Brain Res.* 121, 379-384.
7. Bizzini B., Stoeckel, K. & Schwab, M. (1977) *J. Neurochem.* 28, 529-542.
8. Evinger, O. & Erichsen, J. T. (1986) *Brain Res.* 380, 383-388.
9. Fishman, P. S. & Carrigan, D. R. (1987) Brain Res. 406, 275-279.
10. Manning, K. A., Erichsen, J. T. & Evinger, O. (1990) *Neurosci.* 34, 251-263.
11. Halpern, J. L., Habig, W. H., Neale, E. A. & Stibitz, S. (1990) *Infection and Immunity* 58, 1004-1009.
12. Bizzini, B., Grob, P., Glicksman, M. A. & Akert, K. (1980) *Brain Res.* 193, 221-227.

13. Dobrenis, K., Joseph, A. & Rattazzi, M. G. (1992) *Proc. Natl. Acad. Sci. USA* 89, 2297-2301.
14. Fishman, P. S. & Savitt, J. M. (1989) *Exp. Neurol.* 106, 197-203.
15. Beaude, P., Delacour, A., Bizzini, B., Domuado, D. & Remy, M. H. (1990) *Biochem.* 271, 87-91.
16. Francis, J. W., Hosler, B. H., Brown, R. H., Jr. & Fishman, P. S. (1995) *J. Biol. Chem.* 270, 15434-15442.
17. Fellous. M., Gunther, E., Kemler, R., Weils, J., Berger, R., Guenet, J. L., Jakob, H. & Jacob, F. (1978) *J. Exp. Med.* 148, 58-70.
18. Jakob, H. & Nicolas, J. F. (1987) *Methods Enzymol.* 151, 66-84.
19. Whitehouse, R. L. S., Benichou, J. O. & Ryter, A. (1977) *Biol. Cell.* 30, 155-158.
20. Wojcik, B. E., Nothias, F., Lazar, M., Jouin, H., Nicolas, J. F. & Peschanski, M. (1993) Proc. Natl. *Acad. Sci. USA* 90, 1305-1309.
21. Price, D. L., Griffin, J., Young, A. Peck, K. & Stocks, A. (1975) *Science* 188, 945-947.
22. Matteoli, M., Verderio, C., Rossetto, O., Iezzi, N., Ooco. S., Schiavo, G. & Montecucco, G, (1996) *Proc. Natl. Acad Sci. USA* 93, 13310-13315.
23. Stockel, K., Schwab, M. & Thoenen, H. (1975) *Brain Res.* 99, 1-16.
24. Ugolini, G. (1995a) in *Viral Vectors: Gene Therapy and Neuroscience Applications*, eds. Loewy, A. D. & Kaplitt M. G. (New York: Academic Press), pp. 293-317.
25. Ugolini, G. (1 995b) *The Journal of Comparative Neurology* 356, 457-480.
26. Borke, R. C., Nau, M. E. & R. L Ringler, J. (1983) *Brain Research* 269, 47-55.
27. Horst, G. T. T., Copray, J. C. V. M., liem, R. S. B. & Willigen, J. D. V. (1991) *Neuroscience* 40, 735-758.
28. O'Reilly, P. M. R. & Fitzgerald, M. J. T. (1990) *J. Anat.* 172, 227-243.
29. Chalfie, M., Tu, Y., Euskirchen, G., Ward, W. W. & Prasher, D. C. (1994) *Science* 263, 802-805.
30. Miesenböck, G. & Rothman, J. E. (1997) *Proc. Natl. Acad. Sci. USA* 94, 3402-3407.
31. Le Mouellic, H., Lallemand, Y. & Brûlet, P. (1990) *Proc. Natl. Acad. Sci. USA* 87, 4712-4716.
32. Le Mouellic, H., Lallemand, Y. & Brûlet, P. (1992) *Cell* 69, 251-264.
33. Mombaerts, P., Wang, F., Dulac, C., Chao, S. K., Nemes, A., Mendelsohn, M., Edmondson, J. & Axel, R. (1996) *Cell* 87, 675-686.
34. Mountford, P. S. & Smith, A. G. (1995) *Trends Genet.* 11, 179-184.
35. Rosen, D. R. & al (1993) *Nature* 362, 59-62.
36. Lefebvre, S., Büglen, L., Reboullet, S., Clermont, O., Bûrlet, P., Viollet, L, Benichou, B., Cruaud, O., Millasseau, P., Zeviani, M., Paslier, D. L., Frézal, J., Cohen, D., Weissenbach, J., Munnich, A. & Melki, J. (1995) *Cell* 80, 155-165.
37. Roy, N. & al (1995) *Cell* 80, 167-178.
38. Wolfe, J. H., Deshmane, S. L. & Fraser, N. W. (1992) *Nature genetics* 1, 379-384.
39. Sango, K., Yarmanaka, S., Hoffmann, A., Okuda, Y., Grinberg, A., Westphal, H., McDonald, M. P., Crawley, J. N., Sandhoff, K., Suzuki, K. & Proia, R. L. (1995) *Nature Genetics* 11, 170-176.
40. Duarte, R. G. (1995) *Neurologia* 1, 56-61.
41. Ghadge, G. D., Roos, R. P., Kang, U. J., Wollmann, R., Fishman, P. S., Kalynych, A M., Barr, E. & Leiden, J. M. (1995) *Gene Therapy* 2, 132-137.

What is claimed is:

1. A hybrid fragment of tetanus toxin consisting SEQ ID NO: 2, wherein the hybrid fragment is capable of transferring in vivo an associated protein, a peptide, or a polynucleotide through a neuromuscular junction and at least one synapse.

2. A composition containing an active molecule and the hybrid fragment of tetanus toxin according to claim 1, wherein said active molecule is in association with said hybrid fragment of tetanus toxin.

3. The composition according to claim 2, wherein the active molecule is selected from the group consisting of protein SMN (Survival Motor Neuron), BDNF (brain-derived neurotrophic factor), NT-3 (Neurotrophin 3), NT-4/5 (Neurotrophin 4/5), GDNF (Glial cell-line derived neurotrophic factor), IGF (Insulin-like growth factor), PNI (protease nexin I), SPI3 (Serine Protease Inhibitor protein), ICE (Interleukin-1 Converting Enzyme), Bcl-2, GFP (green fluorescent protein), endonucleases, antibodies, and drugs specifically directed against neurodegenerative diseases.

4. The composition according to claim 2, wherein the active molecule is a polynucleotide encoding a protein.

5. The composition according to claim 4, wherein the polynucleotide further comprises a promoter capable of expression in neurons.

6. The composition according to claim 5, wherein the polynucleotide further comprises an enhancer.

7. The composition according to claim 3, wherein the endonuclease is I-SceI or CRE.

8. The composition according to claim 3, wherein the neurodegenerative disease is latero spinal amyotrophy (LSA).

9. A hybrid fragment of tetanus toxin consisting SEQ ID NO: 2, and a fraction of a fragment A devoid of its toxic activity corresponding to the proteolytic domain having a zinc-binding motif located in the central part of the chain between amino acids 225 and 245, wherein the hybrid fragment is capable of transferring in vivo an associated protein, a peptide or a polynucleotide through a neuromuscular junction and at least one synapse.

10. A composition comprising a hybrid fragment of tetanus toxin consisting of SEQ ID NO: 2, and an associated protein, peptide, or polynucleotide, wherein said protein, peptide or polynucleotide is associated by a covalent or non-covalent linkage, and said composition transfers in vivo said associated protein, peptide or polynucleotide through a neuromuscular junction and at least one synapse.

11. A composition comprising a hybrid fragment of tetanus toxin consisting of SEQ ID NO: 2, and a fraction of a fragment A devoid of its toxic activity corresponding to the proteolytic domain having a zinc-binding motif located in the central part of the chain between amino acids 225 and 245, and an associated protein, peptide, or polynucleotide, wherein said protein, peptide, or polynucleotide is associated by a covalent or non-covalent linkage, and wherein said composition transfers in vivo an associated protein, peptide or polynucleotide through a neuromuscular junction and at least one synapse.

* * * * *

UNITED STATES PATENT AND TRADEMARK OFFICE
CERTIFICATE OF CORRECTION

| | | |
|---|---|---|
| PATENT NO. | : 7,435,792 B2 | Page 1 of 1 |
| APPLICATION NO. | : 09/816467 | |
| DATED | : October 14, 2008 | |
| INVENTOR(S) | : Coen et al. | |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 635 days.

Signed and Sealed this

Twenty-eighth Day of September, 2010

David J. Kappos
*Director of the United States Patent and Trademark Office*

SEQUENCE LISTING

```
<160> NUMBER OF SEQ ID NOS: 19

<210> SEQ ID NO 1
<211> LENGTH: 1600
<212> TYPE: DNA
<213> ORGANISM: Clostridium tetani
<220> FEATURE:
<221> NAME/KEY: CDS
<222> LOCATION: (88)..(1476)

<400> SEQUENCE: 1
ggaaacagct atgaccatga ttacgccaag ctcgaaatta accctcacta aagggaacaa      60
aagctggagc tcggtacccg ggccacc atg gtt ttt tca aca cca att cca ttt    114
                                Met Val Phe Ser Thr Pro Ile Pro Phe
                                  1               5 tct tat tct aaa aat ctg gat tgt tgg gtt gat aat gaa gaa gat ata      162
Ser Tyr Ser Lys Asn Leu Asp Cys Trp Val Asp Asn Glu Glu Asp Ile
 10              15                  20                  25 gat gtt ata tta aaa aag agt aca att tta aat tta gat att aat aat      210
Asp Val Ile Leu Lys Lys Ser Thr Ile Leu Asn Leu Asp Ile Asn Asn
             30                  35                  40 gat att ata tca gat ata tct ggg ttt aat tca tct gta ata aca tat      258
Asp Ile Ile Ser Asp Ile Ser Gly Phe Asn Ser Ser Val Ile Thr Tyr
                 45                  50                  55 cca gat gct caa ttg gtg ccc gga ata aat ggc aaa gca ata cat tta      306
Pro Asp Ala Gln Leu Val Pro Gly Ile Asn Gly Lys Ala Ile His Leu
```

-continued

```
                60                   65                    70
gta aac aat gaa tct tct gaa gtt ata gtg cat aaa gct atg gat att      354
Val Asn Asn Glu Ser Ser Glu Val Ile Val His Lys Ala Met Asp Ile
     75                   80                   85 gaa tat aat gat atg ttt aat aat ttt acc gtt agc ttt tgg ttg agg      402
Glu Tyr Asn Asp Met Phe Asn Asn Phe Thr Val Ser Phe Trp Leu Arg
 90                   95                  100                  105 gtt cct aaa gta tct gct agt cat tta gaa caa tat ggc aca aat gag      450
Val Pro Lys Val Ser Ala Ser His Leu Glu Gln Tyr Gly Thr Asn Glu
             110                  115                  120 tat tca ata att agc tct atg aaa aaa cat agt cta tca ata gga tct      498
Tyr Ser Ile Ile Ser Ser Met Lys Lys His Ser Leu Ser Ile Gly Ser
             125                  130                  135 ggt tgg agt gta tca ctt aaa ggt aat aac tta ata tgg act tta aaa      546
Gly Trp Ser Val Ser Leu Lys Gly Asn Asn Leu Ile Trp Thr Leu Lys
         140                  145                  150 gat tcc gcg gga gaa gtt aga caa ata act ttt agg gat tta cct gat      594
Asp Ser Ala Gly Glu Val Arg Gln Ile Thr Phe Arg Asp Leu Pro Asp
     155                  160                  165 aaa ttt aat gct tat tta gca aat aaa tgg gtt ttt ata act att act      642
Lys Phe Asn Ala Tyr Leu Ala Asn Lys Trp Val Phe Ile Thr Ile Thr
170                  175                  180                  185 aat gat aga tta tct tct gct aat ttg tat ata aat gga gta ctt atg      690
Asn Asp Arg Leu Ser Ser Ala Asn Leu Tyr Ile Asn Gly Val Leu Met
             190                  195                  200 gga agt gca gaa att act ggt tta gga gct att aga gag gat aat aat      738
Gly Ser Ala Glu Ile Thr Gly Leu Gly Ala Ile Arg Glu Asp Asn Asn
             205                  210                  215 ata aca tta aaa cta gat aga tgt aat aat aat aat caa tac gtt tct      786
Ile Thr Leu Lys Leu Asp Arg Cys Asn Asn Asn Asn Gln Tyr Val Ser
         220                  225                  230 att gat aaa ttt agg ata ttt tgc aaa gca tta aat cca aaa gag att      834
Ile Asp Lys Phe Arg Ile Phe Cys Lys Ala Leu Asn Pro Lys Glu Ile
     235                  240                  245 gaa aaa tta tac aca agt tat tta tct ata acc ttt tta aga gac ttc      882
Glu Lys Leu Tyr Thr Ser Tyr Leu Ser Ile Thr Phe Leu Arg Asp Phe
250                  255                  260                  265 tgg gga aac cct tta cga tat gat aca gaa tat tat tta ata cca gta      930
Trp Gly Asn Pro Leu Arg Tyr Asp Thr Glu Tyr Tyr Leu Ile Pro Val
             270                  275                  280 gct tct agt tct aaa gat gtt caa ttg aaa aat ata aca gat tat atg      978
Ala Ser Ser Ser Lys Asp Val Gln Leu Lys Asn Ile Thr Asp Tyr Met
             285                  290                  295 tat ttg aca aat gcg cca tcg tat act aac gga aaa ttg aat ata tat     1026
Tyr Leu Thr Asn Ala Pro Ser Tyr Thr Asn Gly Lys Leu Asn Ile Tyr
         300                  305                  310 tat aga agg tta tat aat gga cta aaa ttt att ata aaa aga tat aca     1074
Tyr Arg Arg Leu Tyr Asn Gly Leu Lys Phe Ile Ile Lys Arg Tyr Thr
     315                  320                  325 cct aat aat gaa ata gat tct ttt gtt aaa tca ggt gat ttt att aaa     1122
Pro Asn Asn Glu Ile Asp Ser Phe Val Lys Ser Gly Asp Phe Ile Lys
330                  335                  340                  345 tta tat gta tca tat aac aat aat gag cac att gta ggt tat ccg aaa     1170
Leu Tyr Val Ser Tyr Asn Asn Asn Glu His Ile Val Gly Tyr Pro Lys
             350                  355                  360 gat gga aat gcc ttt aat aat ctt gat aga att cta aga gta ggt tat     1218
Asp Gly Asn Ala Phe Asn Asn Leu Asp Arg Ile Leu Arg Val Gly Tyr
             365                  370                  375 aat gcc cca ggt atc cct ctt tat aaa aaa atg gaa gca gta aaa ttg     1266
```

-continued

```
Asn Ala Pro Gly Ile Pro Leu Tyr Lys Lys Met Glu Ala Val Lys Leu
        380                 385                 390 cgt gat tta aaa acc tat tct gta caa ctt aaa tta tat gat gat aaa        1314
Arg Asp Leu Lys Thr Tyr Ser Val Gln Leu Lys Leu Tyr Asp Asp Lys
    395                 400                 405 aat gca tct tta gga cta gta ggt acc cat aat ggt caa ata ggc aac        1362
Asn Ala Ser Leu Gly Leu Val Gly Thr His Asn Gly Gln Ile Gly Asn
410                 415                 420                 425 gat cca aat agg gat ata tta att gca agc aac tgg tac ttt aat cat        1410
Asp Pro Asn Arg Asp Ile Leu Ile Ala Ser Asn Trp Tyr Phe Asn His
                430                 435                 440 tta aaa gat aaa att tta gga tgt gat tgg tac ttt gta cct aca gat        1458
Leu Lys Asp Lys Ile Leu Gly Cys Asp Trp Tyr Phe Val Pro Thr Asp
                445                 450                 455 gag gga tgg aca aat gat taaacagatt gatatgttca tgacatatgc               1506
Glu Gly Trp Thr Asn Asp
            460 ccgggatcct ctagagtcga cctcgagggg gggcccggta cccaattcgc cctatagtga      1566 gtcgtattac aattcactgg ccgtcgtttt acaa                                  1600

<210> SEQ ID NO 2
<211> LENGTH: 463
<212> TYPE: PRT
<213> ORGANISM: Clostridium tetani

<400> SEQUENCE: 2

Met Val Phe Ser Thr Pro Ile Pro Phe Ser Tyr Ser Lys Asn Leu Asp
  1               5                  10                  15

Cys Trp Val Asp Asn Glu Glu Asp Ile Asp Val Ile Leu Lys Lys Ser
                 20                  25                  30

Thr Ile Leu Asn Leu Asp Ile Asn Asn Asp Ile Ile Ser Asp Ile Ser
             35                  40                  45

Gly Phe Asn Ser Ser Val Ile Thr Tyr Pro Asp Ala Gln Leu Val Pro
         50                  55                  60

Gly Ile Asn Gly Lys Ala Ile His Leu Val Asn Asn Glu Ser Ser Glu
 65                  70                  75                  80

Val Ile Val His Lys Ala Met Asp Ile Glu Tyr Asn Asp Met Phe Asn
                 85                  90                  95

Asn Phe Thr Val Ser Phe Trp Leu Arg Val Pro Lys Val Ser Ala Ser
                100                 105                 110

His Leu Glu Gln Tyr Gly Thr Asn Glu Tyr Ser Ile Ile Ser Ser Met
            115                 120                 125

Lys Lys His Ser Leu Ser Ile Gly Ser Gly Trp Ser Val Ser Leu Lys
        130                 135                 140

Gly Asn Asn Leu Ile Trp Thr Leu Lys Asp Ser Ala Gly Glu Val Arg
145                 150                 155                 160

Gln Ile Thr Phe Arg Asp Leu Pro Asp Lys Phe Asn Ala Tyr Leu Ala
                165                 170                 175

Asn Lys Trp Val Phe Ile Thr Ile Thr Asn Asp Arg Leu Ser Ser Ala
            180                 185                 190

Asn Leu Tyr Ile Asn Gly Val Leu Met Gly Ser Ala Glu Ile Thr Gly
        195                 200                 205

Leu Gly Ala Ile Arg Glu Asp Asn Asn Ile Thr Leu Lys Leu Asp Arg
    210                 215                 220

Cys Asn Asn Asn Asn Gln Tyr Val Ser Ile Asp Lys Phe Arg Ile Phe
225                 230                 235                 240
```

```
Cys Lys Ala Leu Asn Pro Lys Glu Ile Glu Lys Leu Tyr Thr Ser Tyr
            245                 250                 255

Leu Ser Ile Thr Phe Leu Arg Asp Phe Trp Gly Asn Pro Leu Arg Tyr
            260                 265                 270

Asp Thr Glu Tyr Tyr Leu Ile Pro Val Ala Ser Ser Lys Asp Val
        275                 280                 285

Gln Leu Lys Asn Ile Thr Asp Tyr Met Tyr Leu Thr Asn Ala Pro Ser
            290                 295                 300

Tyr Thr Asn Gly Lys Leu Asn Ile Tyr Tyr Arg Arg Leu Tyr Asn Gly
305                 310                 315                 320

Leu Lys Phe Ile Ile Lys Arg Tyr Thr Pro Asn Asn Glu Ile Asp Ser
            325                 330                 335

Phe Val Lys Ser Gly Asp Phe Ile Lys Leu Tyr Val Ser Tyr Asn Asn
            340                 345                 350

Asn Glu His Ile Val Gly Tyr Pro Lys Asp Gly Asn Ala Phe Asn Asn
            355                 360                 365

Leu Asp Arg Ile Leu Arg Val Gly Tyr Asn Ala Pro Gly Ile Pro Leu
            370                 375                 380

Tyr Lys Lys Met Glu Ala Val Lys Leu Arg Asp Leu Lys Thr Tyr Ser
385                 390                 395                 400

Val Gln Leu Lys Leu Tyr Asp Asp Lys Asn Ala Ser Leu Gly Leu Val
            405                 410                 415

Gly Thr His Asn Gly Gln Ile Gly Asn Asp Pro Asn Arg Asp Ile Leu
            420                 425                 430

Ile Ala Ser Asn Trp Tyr Phe Asn His Leu Lys Asp Lys Ile Leu Gly
            435                 440                 445

Cys Asp Trp Tyr Phe Val Pro Thr Asp Glu Gly Trp Thr Asn Asp
            450                 455                 460

<210> SEQ ID NO 3
<211> LENGTH: 1392
<212> TYPE: DNA
<213> ORGANISM: Clostridium tetani

<400> SEQUENCE: 3 atggttttt caacaccaat tccattttct tattctaaaa atctggattg ttgggttgat      60
aatgaagaag atatagatgt tatattaaaa aagagtacaa ttttaaattt agatattaat     120
aatgatatta tatcagatat atctggggtt aattcatctg taataacata tccagatgct     180
caattggtgc ccggaataaa tggcaaagca atacatttag taaacaatga atcttctgaa     240
gttatagtgc ataaagctat ggatattgaa tataatgata tgtttaataa ttttaccgtt     300
agcttttggt tgagggttcc taaagtatct gctagtcatt tagaacaata tggcacaaat     360
gagtattcaa taattagctc tatgaaaaaa catagtctat caataggatc tggttggagt     420
gtatcactta aggtaataaa cttaatatgg actttaaaag attccgcggg agaagttaga     480
caaataactt ttagggattt acctgataaa tttaatgctt atttagcaaa taatgggtt      540
tttataacta ttactaatga tagattatct tctgctaatt tgtatataaa tggagtactt     600
atgggaagtg cagaaattac tggtttagga gctattagag aggataataa tataacatta     660
aaactagata gatgtaataa taataatcaa tacgtttcta ttgataaatt taggatattt     720
tgcaaagcat taaatccaaa agagattgaa aaattataca caagttattt atctataacc     780
tttttaagag acttctgggg aaaccctta cgatatgata cagaatatta tttaatacca    840
```

-continued

```
gtagcttcta gttctaaaga tgttcaattg aaaaatataa cagattatat gtatttgaca      900
aatgcgccat cgtatactaa cggaaaattg aatatatatt atagaaggtt ataataatgga     960 ctaaaattta ttataaaaag atatacacct aataatgaaa tagattcttt tgttaaatca     1020
ggtgatttta ttaaattata tgtatcatat aacaataatg agcacattgt aggttatccg     1080
aaagatggaa atgcctttaa taatcttgat agaattctaa gagtaggtta taatgcccca     1140
ggtatccctc tttataaaaa aatggaagca gtaaaattgc gtgatttaaa aacctattct     1200
gtacaactta aattatatga tgataaaaat gcatctttag gactagtagg tacccataat     1260
ggtcaaatag gcaacgatcc aaataggat atattaattg caagcaactg gtactttaat      1320
catttaaaag ataaaatttt aggatgtgat tggtactttg tacctacaga tgagggatgg     1380
acaaatgatt aa                                                         1392
```

<210> SEQ ID NO 4
<211> LENGTH: 49
<212> TYPE: DNA
<213> ORGANISM: Artificial Sequence
<220> FEATURE:
<223> OTHER INFORMATION: Description of Artificial Sequence: Primer

<400> SEQUENCE: 4

```
cccccgggc caccatggtt ttttcaacac caattccatt ttcttattc                    49
```

<210> SEQ ID NO 5
<211> LENGTH: 18
<212> TYPE: DNA
<213> ORGANISM: Artificial Sequence
<220> FEATURE:
<223> OTHER INFORMATION: Description of Artificial Sequence: Primer

<400> SEQUENCE: 5

```
ctaaaccagt aatttctg                                                    18
```

<210> SEQ ID NO 6
<211> LENGTH: 25
<212> TYPE: DNA
<213> ORGANISM: Artificial Sequence
<220> FEATURE:
<223> OTHER INFORMATION: Description of Artificial Sequence: Primer

<400> SEQUENCE: 6

```
aattatggac tttaaaagat tccgc                                            25
```

<210> SEQ ID NO 7
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 7

```
ggcattataa cctactctta gaat                                             24
```

<210> SEQ ID NO 8
<211> LENGTH: 27
<212> TYPE: DNA
<213> ORGANISM: Artificial Sequence
<220> FEATURE:
<223> OTHER INFORMATION: Description of Artificial Sequence: Primer

<400> SEQUENCE: 8

```
aatgccttta ataatcttga tagaaat                                          27
```

<210> SEQ ID NO 9
<211> LENGTH: 41
<212> TYPE: DNA
<213> ORGANISM: Artificial Sequence
<220> FEATURE:
<223> OTHER INFORMATION: Description of Artificial Sequence: Primer

<400> SEQUENCE: 9 cccccccgggc atatgtcatg aacatatcaa tctgtttaat c        41

<210> SEQ ID NO 10
<211> LENGTH: 12
<212> TYPE: DNA
<213> ORGANISM: Unknown Organism
<220> FEATURE:
<223> OTHER INFORMATION: Description of Unknown Organism: Construct
      pCMV.LACZ.TTC

<400> SEQUENCE: 10
tagttattaa ta                                         12

<210> SEQ ID NO 11
<211> LENGTH: 12
<212> TYPE: DNA
<213> ORGANISM: Unknown Organism
<220> FEATURE:
<223> OTHER INFORMATION: Description of Unknown Organism: Construct
      pCMV.LACZ.TTC

<400> SEQUENCE: 11
accgccatgc at                                         12

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence: Primer

<400> SEQUENCE: 12
ctgaatatcg acggtttcca tatg                            24

<210> SEQ ID NO 13
<211> LENGTH: 40
<212> TYPE: DNA
<213> ORGANISM: Artificial Sequence
<220> FEATURE:
<223> OTHER INFORMATION: Description of Artificial Sequence: Primer

<400> SEQUENCE: 13
ggcagtctcg agtctagacc atggcttttt gacaccagac           40

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Linker

<400> SEQUENCE: 14
catgactggg gatccccagt                                 20

<210> SEQ ID NO 15
<211> LENGTH: 24
<212> TYPE: DNA

-continued

```
<213> ORGANISM: Artificial Sequence
<220> FEATURE:
<223> OTHER INFORMATION: Description of Artificial Sequence: Primer

<400> SEQUENCE: 15
tatgataaaa atgcatcttt agga                                          24

<210> SEQ ID NO 16
<211> LENGTH: 37
<212> TYPE: DNA
<213> ORGANISM: Artificial Sequence
<220> FEATURE:
<223> OTHER INFORMATION: Description of Artificial Sequence: Primer

<400> SEQUENCE: 16
tggagtcgac gctagcagga tcatttgtcc atccttc                            37

<210> SEQ ID NO 17
<211> LENGTH: 17
<212> TYPE: DNA
<213> ORGANISM: Artificial Sequence
<220> FEATURE:
<223> OTHER INFORMATION: Description of Artificial Sequence: Linker

<400> SEQUENCE: 17
gatatcggcg cgccagc                                                  17

<210> SEQ ID NO 18
<211> LENGTH: 17
<212> TYPE: DNA
<213> ORGANISM: Artificial Sequence
<220> FEATURE:
<223> OTHER INFORMATION: Description of Artificial Sequence: Linker

<400> SEQUENCE: 18
tggcgcgccg atatcgc                                                  17

<210> SEQ ID NO 19
<211> LENGTH: 14
<212> TYPE: DNA
<213> ORGANISM: Artificial Sequence
<220> FEATURE:
<223> OTHER INFORMATION: Description of Artificial Sequence: Linker

<400> SEQUENCE: 19
tcgatggcgc gcca                                                     14
```